United States Patent
Kuusela et al.

(10) Patent No.: US 11,056,240 B2
(45) Date of Patent: *Jul. 6, 2021

(54) RADIATION THERAPY PLANNING USING INTEGRATED MODEL

(71) Applicant: Varian Medical Systems International AG., Cham (CH)

(72) Inventors: Esa Kuusela, Espoo (FI); Maria Cordero Marcos, Espoo (FI); Joona Hartman, Espoo (FI); Jarkko Y Peltola, Tuusula (FI); Janne I Nord, Espoo (FI)

(73) Assignee: Varian Medical Systems International AG, Cham (CH)

( * ) Notice: Subject to any disclaimer, the term of this patent is extended or adjusted under 35 U.S.C. 154(b) by 1319 days.

This patent is subject to a terminal disclaimer.

(21) Appl. No.: 15/258,748

(22) Filed: Sep. 7, 2016

(65) Prior Publication Data
US 2016/0378948 A1    Dec. 29, 2016

Related U.S. Application Data

(63) Continuation of application No. 14/039,920, filed on Sep. 27, 2013, now Pat. No. 9,463,334.

(Continued)

(51) Int. Cl.
*G16H 50/50* (2018.01)
*G06N 5/00* (2006.01)
(Continued)

(52) U.S. Cl.
CPC .............. *G16H 50/50* (2018.01); *A61N 5/103* (2013.01); *G06F 19/00* (2013.01); *G06N 5/00* (2013.01);
(Continued)

(58) Field of Classification Search
CPC ....................................................... G06N 20/00
See application file for complete search history.

(56) References Cited

U.S. PATENT DOCUMENTS

| | | |
|---|---|---|
| 5,859,891 A | 1/1999 | Hibbard |
| 2008/0310590 A1 | 12/2008 | Meyer et al. |

(Continued)

FOREIGN PATENT DOCUMENTS

| | | |
|---|---|---|
| CN | 101467155 A | 6/2009 |
| CN | 102132279 A | 7/2011 |

(Continued)

OTHER PUBLICATIONS

A. Agrawal et al., "A lung cancer outcome calculator using ensemble data mining on SEER data", ACM Int'l Workshop on Data Mining in Bioinformatics (BIOKDD), Aug. 2011, 9 pages. (Year: 2011).*

(Continued)

*Primary Examiner* — Vincent Gonzales

(57) ABSTRACT

System and method for automatically generate therapy plan parameters by use of an integrate model with extended applicable regions. The integrated model integrates multiple predictive models from which a suitable predictive model can be selected automatically to perform prediction for a new patient case. The integrated model may operate to evaluate prediction results generated by each predictive model and the associated prediction reliabilities and selectively output a satisfactory prediction. Alternatively, the integrated model may select a suitable predictive model by a decision hierarchy in which each level corresponds to divisions of a patient data feature set and divisions on a subordinate level are nested with divisions on a superordinate level.

19 Claims, 9 Drawing Sheets

Related U.S. Application Data

(60) Provisional application No. 61/793,655, filed on Mar. 15, 2013.

(51) Int. Cl.
*G06F 19/00* (2018.01)
*A61N 5/10* (2006.01)
*G06N 5/02* (2006.01)

(52) U.S. Cl.
CPC ...... *G06N 5/022* (2013.01); *A61N 2005/1041* (2013.01)

(56) References Cited

U.S. PATENT DOCUMENTS

| | | |
|---|---|---|
| 2009/0234627 A1 | 9/2009 | Yu et al. |
| 2010/0232572 A1 | 9/2010 | Nord et al. |
| 2011/0106749 A1 | 5/2011 | Krishnan et al. |
| 2012/0014507 A1 | 1/2012 | Wu et al. |
| 2012/0158624 A1 | 6/2012 | Lingenfelder et al. |

FOREIGN PATENT DOCUMENTS

| | | |
|---|---|---|
| WO | 2010036732 A1 | 4/2010 |
| WO | 2011153639 A2 | 12/2011 |
| WO | 2012085722 A1 | 6/2012 |

OTHER PUBLICATIONS

T. Willoughby, et al., "Evaluation ans Scoring of Radiotherapy Treatment Plans Using an Artificial Neural Network", Int. J. Radiation Oncology Biol. Phys., vol. 34, No. 4, pp. 923-930, 1996.

S. Russell and P. Norvig, Artificial Intelligence: A Modern Approach, 2nd Ed., 2003, pp. 649-789.

E. Shortliffe, et al., "Knoledge Engineering for Medical Decision Making: A Review of Computer-based Clinical Decision Aids", Proc. IEEE, vol. 67, No. 9, Sep. 1979, pp. 1207-1224.

An Integrated Two-Level Hierarchical System for Decision Making in Radiation Therapy Based on Fuzzy Cognitive Maps; IEEE Transactions on Biomedical Engineering, vol. 50, No. 12, Dec. 2013, Groumpos, et al.; pp. 1326-1339.

Predicting Dose-Volumes Histograms for Organs-at-Risk in IMRT Planning; Med. Phys. 39; p. 7449-7461; Appenzoller, et al.; Published Nov. 27, 2012.

Quantitive Analysis of the Factors Which Affect the Interpatient Organ-at-Risk Dose Sparing Variation in IMRT Plans; Med. Phys. 39; p. 6868-6879; Yuan, et al.; Published Oct. 23, 2012.

An Integrated Two-Level Hierarchical System for Decision Making in Radiation Therapy Based on Fuzzy Cognitive Maps; IEEE Transactions on Biomedical Engineering, vol. 50, No. 12, Dated Dec. 12, 2003; Papageorgiou, et al.; p. 1326-1339.

\* cited by examiner

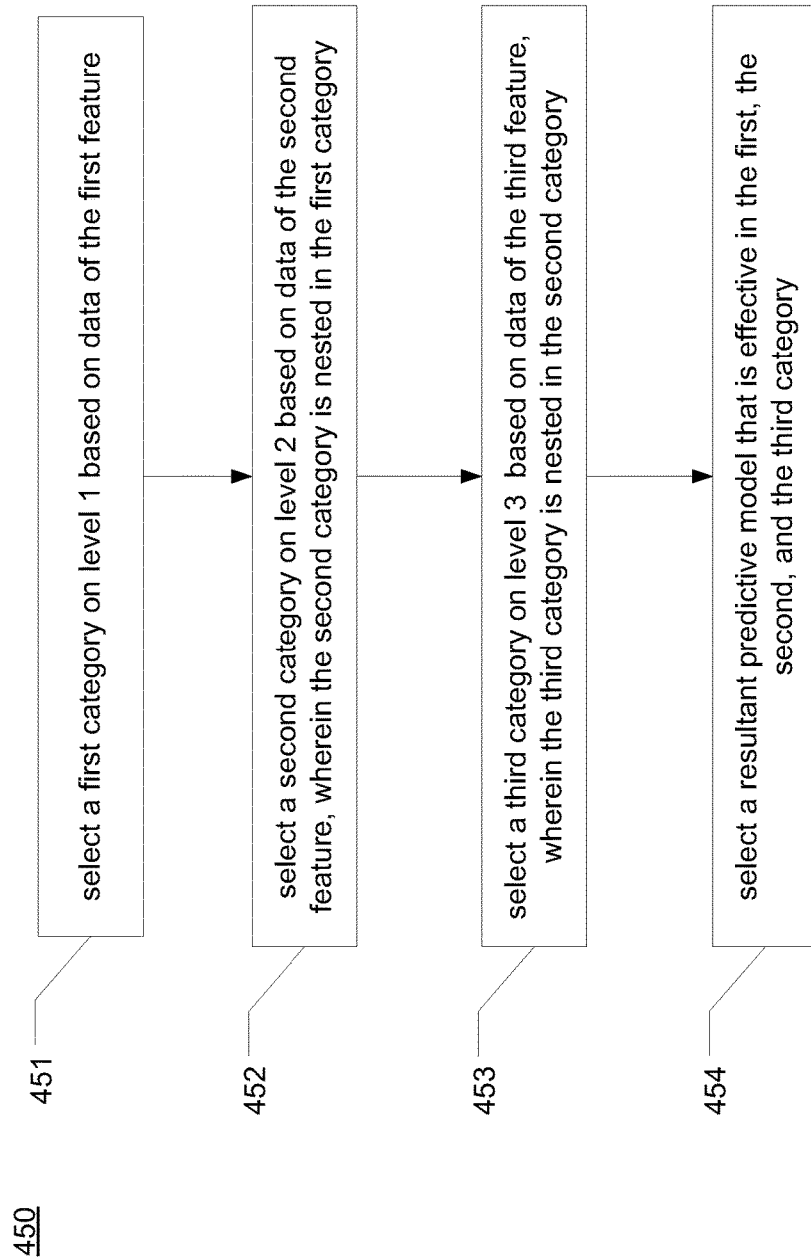

RADIATION THERAPY PLANNING USING INTEGRATED MODEL

CROSS REFERENCE

The present application is a continuation application of U.S. patent application Ser. No. 14/039,920, filed on Sep. 27, 2013, entitled "RADIATION THERAPY PLANNING USING INTEGRATED MODEL," now U.S. Pat. No. 9,463,334, which claims priority to U.S. Provisional Patent Application No. 61/793,655, entitled "PROTECTING ACHIEVABLE DOSE USING HIERARCHICAL KNOWLEDGE BASED MODELS," filed on Mar. 15, 2013. The foregoing patent applications are hereby incorporated by reference in their entireties for all purposes.

TECHNICAL FIELD

Embodiments of the present disclosure relate generally to medical devices, and more particularly, to radiation therapy devices.

BACKGROUND

In knowledge-based medical treatment planning, the information of existing plans can be used to make a treatment plan for a new patient, e.g., by estimating an achievable dose distribution. A prediction can be made by distilling patient geometry and dose information of multiple previous clinical plans into a prediction model that can be used for dose prediction without storing all information from the original set of plans.

Such a knowledge-based model could have various implementations. For example, it could be a regression model associating geometric parameters to dosimetric parameters. Typically a certain model derived from a training set only has a limited region, e.g., with respect to geometric parameters of a tumor, in which its predictions are valid. If the geometric parameters of the new case differ too much of the geometric parameters spanned by the training set, the dose predictions unfortunately can become unreliable.

A clinic usually has several predictive models that collectively can cover a large variety of different regions. Conventionally, a therapy expert, e.g., an oncologist, has to manually explore the available models and thereby determine one for prediction computation based on a personal judgment. This manual selection process can be time consuming and possibly unreliable, especially when the number of available models is large, and each model corresponds to a complicated geometric parameter set.

SUMMARY OF THE INVENTION

Therefore, it would be advantageous to provide a therapy planning mechanism that can make valid predictions over extended regions in an automated and systematic manner.

Accordingly, embodiment of the present disclosure employs an integrated model that combines multiple predictive models from which a resultant predictive model can be selected automatically to perform prediction for a new patient case. The multiple predictive models are trained from existing clinical data and cover varieties of valid or effective regions with respect to patient data pertaining to radiation therapy. The integrated model comprises a model selection module and an individual predictive model module. The model selection module may operate to evaluate prediction results generated by each predictive model and the associated prediction reliabilities and thereby selectively output one or more satisfactory predictions. Alternatively, the model selection module may comprise a decision hierarchy in which each level corresponds to divisions of a patient data feature set. The divisions on a subordinate level are nested with divisions on a superordinate level. The integrated model may be generated automatically, e.g., by configuring multiple models from a single training dataset in accordance with a hierarchical clustering algorithm. Therefore, the integrated model advantageously can cover extended effective regions for therapy prediction without the need for manual selection of a suitable model.

In one embodiment of the present disclosure, a computer implemented method of automatically generating a radiation treatment plan for a patient comprises: (1) accessing patient information pertaining to a radiation treatment for a patient; (2) automatically selecting one or more predictive models based on the patient information in accordance with a hierarchical model comprising a plurality of predictive models arranged in a hierarchy, wherein each of the predictive model is established based on training data and operable to generate a radiation treatment prediction; (3) processing the patient information in accordance with the one or more predictive model; and (4) outputting one or more radiation treatment predictions.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

Embodiments of the present invention will be better understood from a reading of the following detailed description, taken in conjunction with the accompanying drawing figures in which like reference characters designate like elements and in which:

FIG. 4B is a flow charge depicting an exemplary method of selecting a suitable predictive model in a hierarchical model in accordance with an embodiment of the present disclosure.

DETAILED DESCRIPTION

Figure 1:
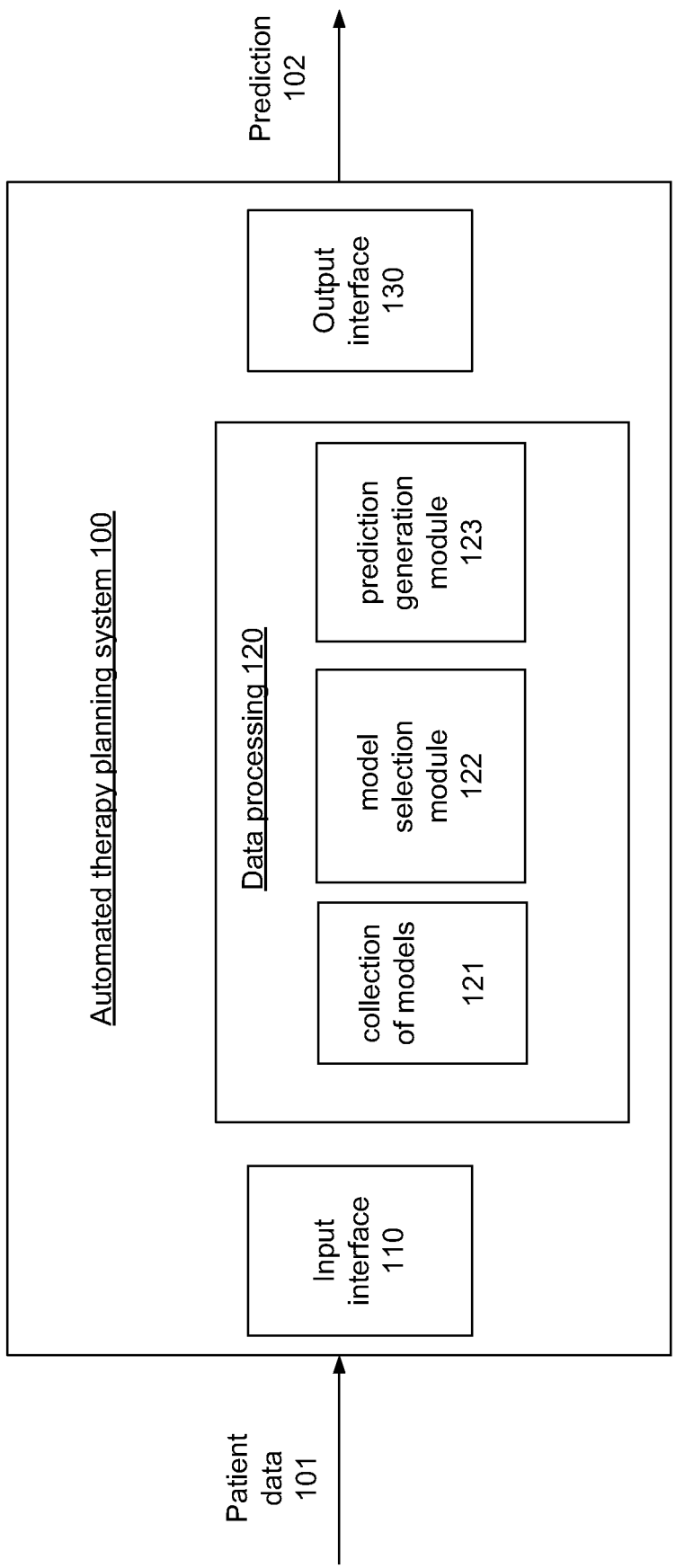
FIG. 1 is a function block diagram illustrating an exemplary configuration of an automated therapy planning system including a collection of predictive sub-models and a model selection module in accordance with an embodiment of the present disclosure

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Notation and Nomenclature:

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

Radiation Therapy Planning Using Integrated Model

FIG. 1 is a function block diagram illustrating an exemplary configuration of an automated therapy planning system 100 including a collection of predictive models 121 and a model selection module 122 in accordance with an embodiment of the present disclosure. The system 100 includes an input interface 110 to receive patient data, a data processing component 120 that implements an integrated model and includes a collection of predictive sub-models 121, a model selection module 122 and prediction generation module 125, and an output interface 130. The system 100 in whole or in part may be implemented as a software program, hardware logic, or a combination thereof.

Each predictive sub-model in the collection 121 may only be applicable to limited regions with respect to the patient data features, e.g., geometric parameters, contained in the patient data 101. For instance, depending on the applicable regions encompassed by the training data, a sub-model may be determined to be valid to predict for high risk prostate cancer with a tumor size within a certain range; while another sub-model may be determined to be effective to predict for low risk prostate cancer with a tumor size within another range. The individual predictive models are combined into an integrated model capable of automatically selecting an applicable sub-model for a specific set of patient data, as will be described in greater detail below.

During operation, based on the patient data 101 provided through the input interface 110, the model selection module 122 can automatically select a suitable sub-model from the collection of sub-models 121. The selected sub-model is used to generate a prediction at the prediction generation module 123 and output the results through the output interface 130. By virtue of an automatic sub-model selection process that may be transparent to a user, e.g., a therapy planner, the integrated model advantageously can cover extended effective regions for therapy prediction without the need for manual selection of a suitable sub-model. In some embodiments, the system may comprise a user interface that allows a user to narrow down the sub-model search scope by user-defined constraints. A set of patient data typically includes multiple data points. As will be appreciated by those skilled in the art, the present disclosure is not limited to any mechanism or criteria of determining a matching sub-model based on patient data. For example, a sub-model may be selected because a predetermined number of points of the patient data fall in the effective regions of the sub-model. In some embodiments, each sub-model has its own training set, e.g., a set of pre-treated patient cases, the matching criteria for a new patient case may be a certain similarity metric between the new single case and the training set. For example, a comparison between parameters of the new patient case and the mean value of the same parameters in the training set can be used as a similarity metric. The selection could be based on maximum similarity, e.g., only one sub-model is selected, the one with the highest score in the chosen similarity metric. The sub-model selection could also be based on a certain acceptable similarity level, e.g., the number of selected sub-model could differ, when all sub-models with a high enough similarity metric score are selected.

The input patient data may contain any combination of parameters that can practically affect the therapy in a manner that is well known in the art. For example, the patient data may be organized as a vector or a data structure comprising feature elements of target size, organ at risk sizes organ shape descriptions, partial target volumes overlapping one organ, partial target volumes overlapping multiple organs, partial organ volumes overlapping the target, partial organ volumes overlapping other organs, and etc.

As will be appreciated by those skilled in the art, the present disclosure is not limited to any specific mechanism of generating individual sub-models or any specific collection of sub-models. For example, the sub-models encompassed by an integrated model in accordance with the present disclosure may be resulted from any curve fitting technique that is well known in the art. Specifically, the curve fitting may be based on a regression analysis such as linear regression, interpolation, or non-linear regression, e.g., major axis, reduced major axis, polynomial, exponential, logarithmic power, and etc.

The individual sub-models may originate from a clinic having several models to cover different regions, or developed by radiation equipment provider, or are shared among several clinics. The models may be derived from published literature data or clinical data as submitted by clinic practitioners. As will be appreciated by those skilled in the art, the models may be shared either without or without providing the actual patient data related to the training set used to train the model. The models may be used without accessing the original patient data used for training. In some embodiments, a certain clinic or other model provider can simultaneously create all sub-models to be used together, or produces an integrated model by combining several previously training sub-models together. In the latter case, some or all sub-models may have been obtaining from other parties. In some embodiments, the sub-model training can be done based on training set in a cloud. In some embodiments, several sub-models are made available in a cloud and a software component may be used to search a suitable sub-model from the cloud.

The present disclosure may be applied in association with any type of radiation therapy in conjunction with any type of radiation therapy equipment, such as intensity modulated radiation therapy (IMRT), photon therapy, charged particle therapy, and etc. As will be appreciated by those skilled in the art, the present disclosure is not limited to any specific type of results that can be derived from an integrated model and individual sub-models. The planning system can also produce, for example, dose predictions to the tumor and normal tissue achieved by a radiation therapy system, or corresponding operating parameters of a particular radiation therapy equipment. For example, in radiation therapy planning for IMRT, the objective is usually to estimate a set of parameters to control a radiation therapy device for delivering radiation to a patient. Such a system may also predict chance of survival, or chance of complication. The output may be use to feed to a downstream optimization system prior to use according to any optimization technique that is well known in the art.

Figure 2:
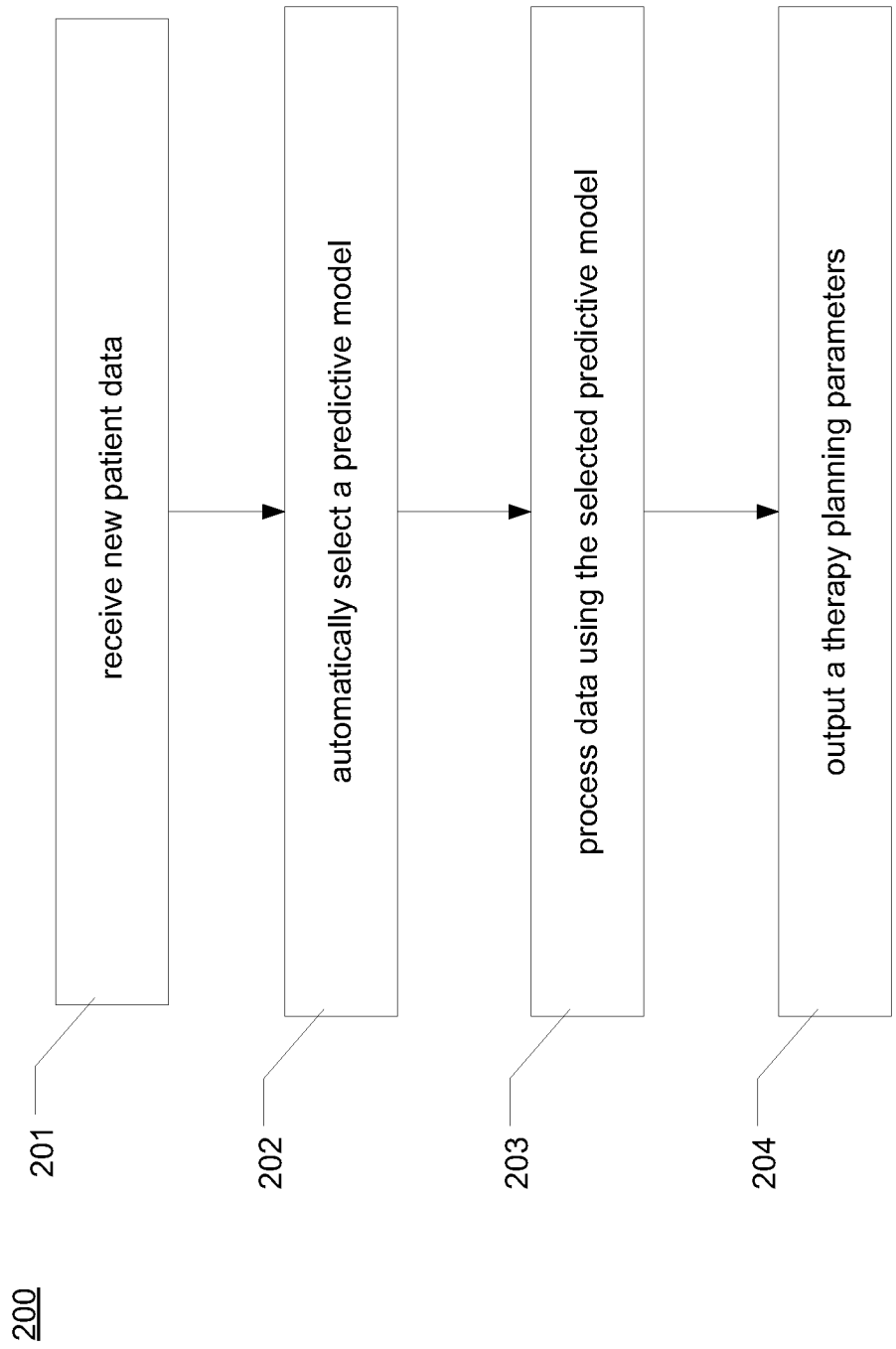
FIG. 2 is a flow chart illustrating an exemplary method of automatic therapy planning in accordance with an embodiment of the present disclosure.

FIG. 2 is a flow chart illustrating an exemplary method 200 of automatic therapy planning in accordance with an embodiment of the present disclosure. Method 200 may be implemented as a system illustrated in FIG. 1. At 201, a set of new patient data is received to a system that employs an integrated sub-model. At 202, one or more suitable sub-models can be automatically selected by the integrated model based on the received patient data. The selected sub-model can be used to process the new patient data at 203 and output a set of therapy planning parameters at 204.

Figure 3A:
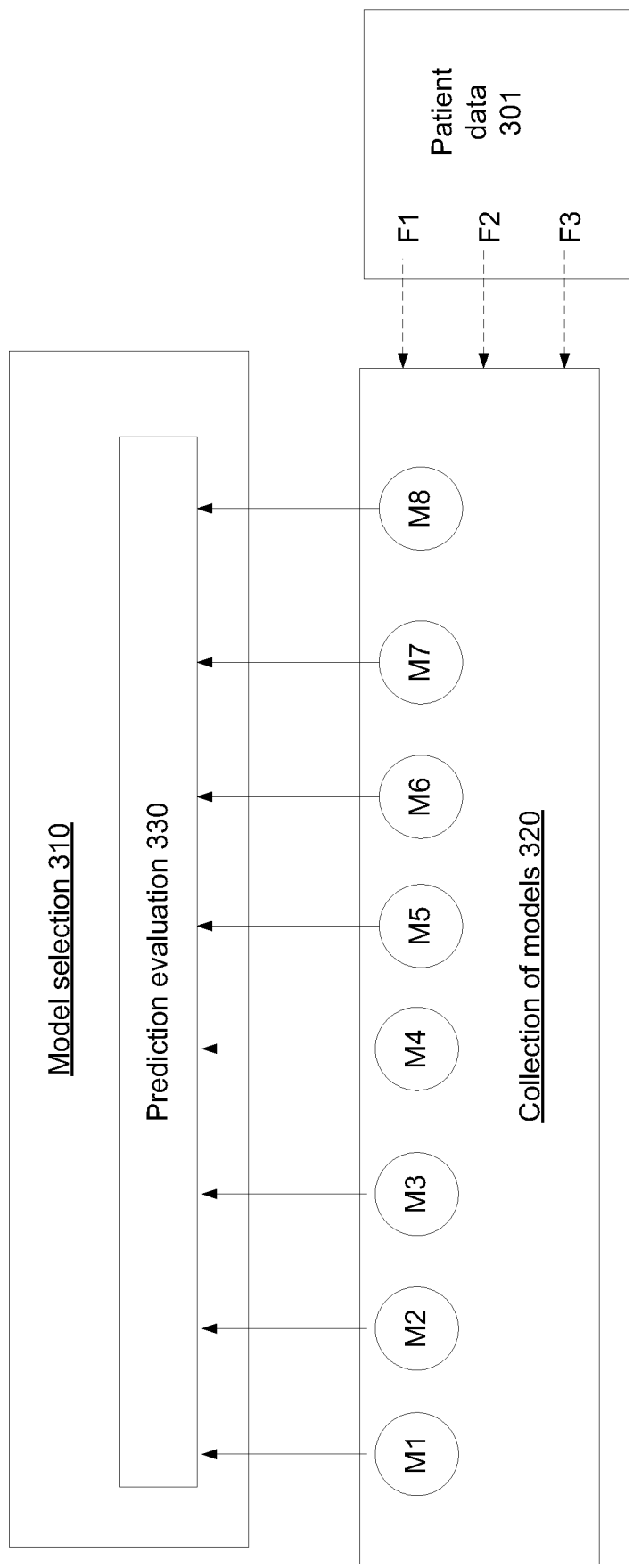
FIG. 3A is a diagram illustrating an exemplary configuration of an integrated model configured to determine a suitable predictive model by virtue of evaluation in accordance with an embodiment of the present disclosure.

FIG. 3A is a diagram illustrating an exemplary configuration of an integrated model operable to determine a suitable sub-model by virtue of evaluation in accordance with an embodiment of the present disclosure. In this example, the integrated model comprises a two-level hierarchical structure. The first level is a model selection component. The second level is a collection of sub-models 320, e.g., M1-M8, with limited application regions with respect to the parameters contained in the patient data. The patient data 301 is provided to the predictive models 320 and processed thereby. In some embodiments, regardless of the respective applicable regions, each sub-model can yield a prediction result, e.g., achievable dose distribution prediction, accompanied with parameters indicative of the quality of the prediction, such as reliability of the result, e.g., affected by the internal coherence of the training set, complexity of the predicted plan, and probability of the result. In some other embodiments, data indicating reliability of a sub-model based on comparison between the prediction made by the sub-model and the actual outcome of the treatment by use of the prediction its can be included in the evaluation metrics.

The outputs of the predictive models M1-M8 are furnished to the prediction evaluation component 330 that is configured to comprehensively evaluate the corresponding prediction results and the quality indicators in accordance with predefined criteria or a ranking mechanism. Thereby, the model selection module 310 can output the results generated by the predictive models that meet the predefined criteria. It will be appreciated by those skilled in the art that the present disclosure is not limited to any specific evaluation measure.

Figure 3B:
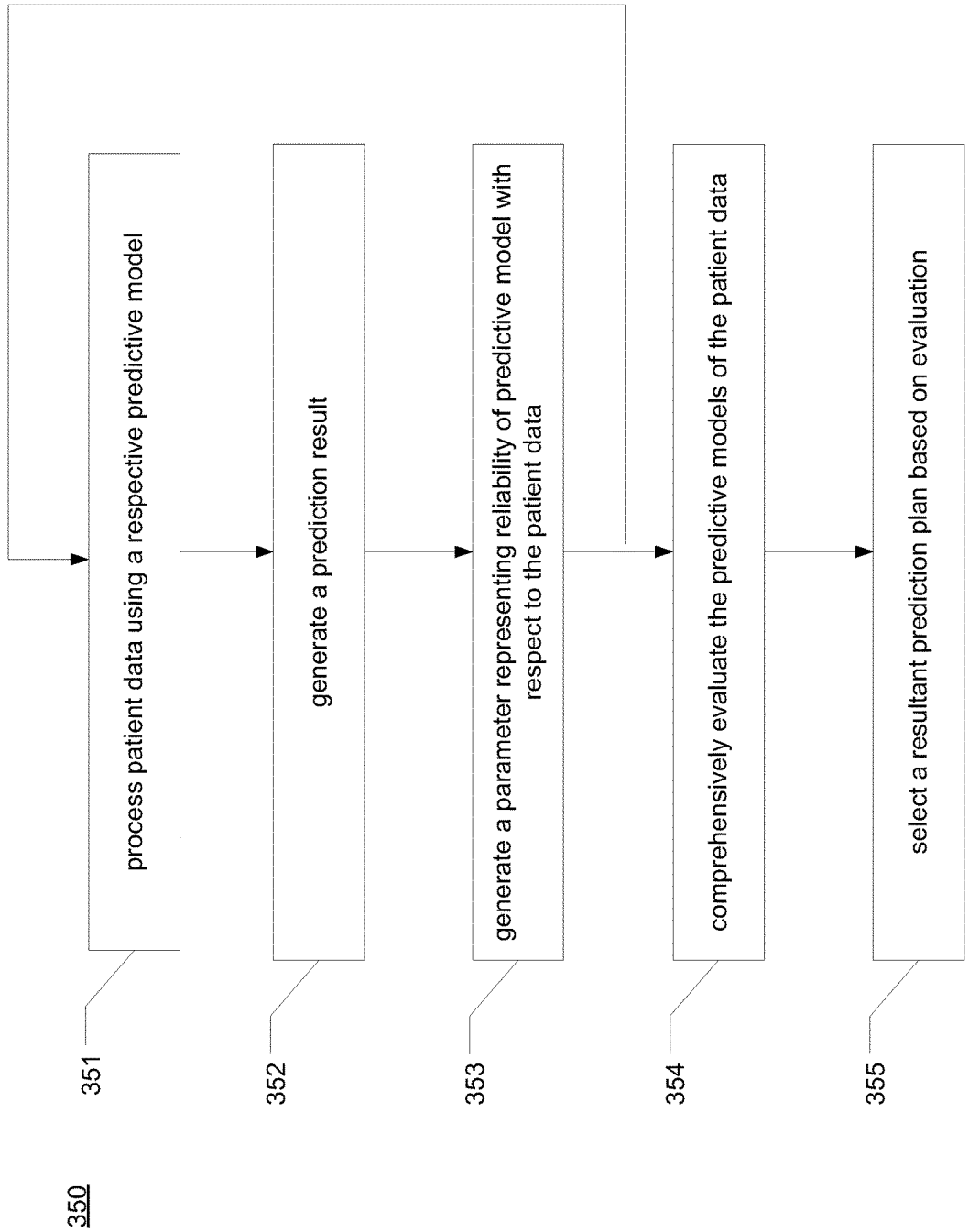
FIG. 3B is a flow chart depicting an exemplary method of automatic therapy planning by employing an integrated model in which a suitable predictive model can be determined by virtue of evaluation in accordance with an embodiment of the present disclosure.

FIG. 3B is a flow chart depicting an exemplary method 350 of automatic therapy planning by employing an integrated model in which a suitable predictive sub-model can be determined by virtue of evaluation in accordance with an embodiment of the present disclosure. A respective predictive model contained in the integrated model processes the input patient data at 351 and generates a prediction result at 352. At 353, the sub-model can also generate a parameter representing reliability of the prediction result with respect to the patient data. The process described in 351-353 is repeated for all sub-models or a subset of models in the integrated model, which can be performed either simultaneously or sequentially. If performed one at a time, it may be that all sub-models are evaluated or some sub-set of them. The results are then evaluated comprehensively with respect to the input patient data at 354 in accordance with predetermined criteria. An automated evaluation process may include determining the quality (e.g., accuracy or reliability) of the prediction. It can also be based on trying automatic planning based on automatically generated instructions to plan optimizer (e.g., automatically generated optimization objectives), and evaluating the clinical quality of the automatically created plans, At 355, a resultant prediction plan can be selected based on the evaluation and may be used for further evaluation. As described above, parameters indicative of the quality of the prediction, such as reliability of the result based on comparison between the prediction made by the sub-model and the actual outcome of the treatment by use of the prediction, complexity of the predicted plan, and probability of the result can all be incorporated for the evolution process. The evaluation criteria may be determined by radiation therapy experts for example.

Figure 4A:
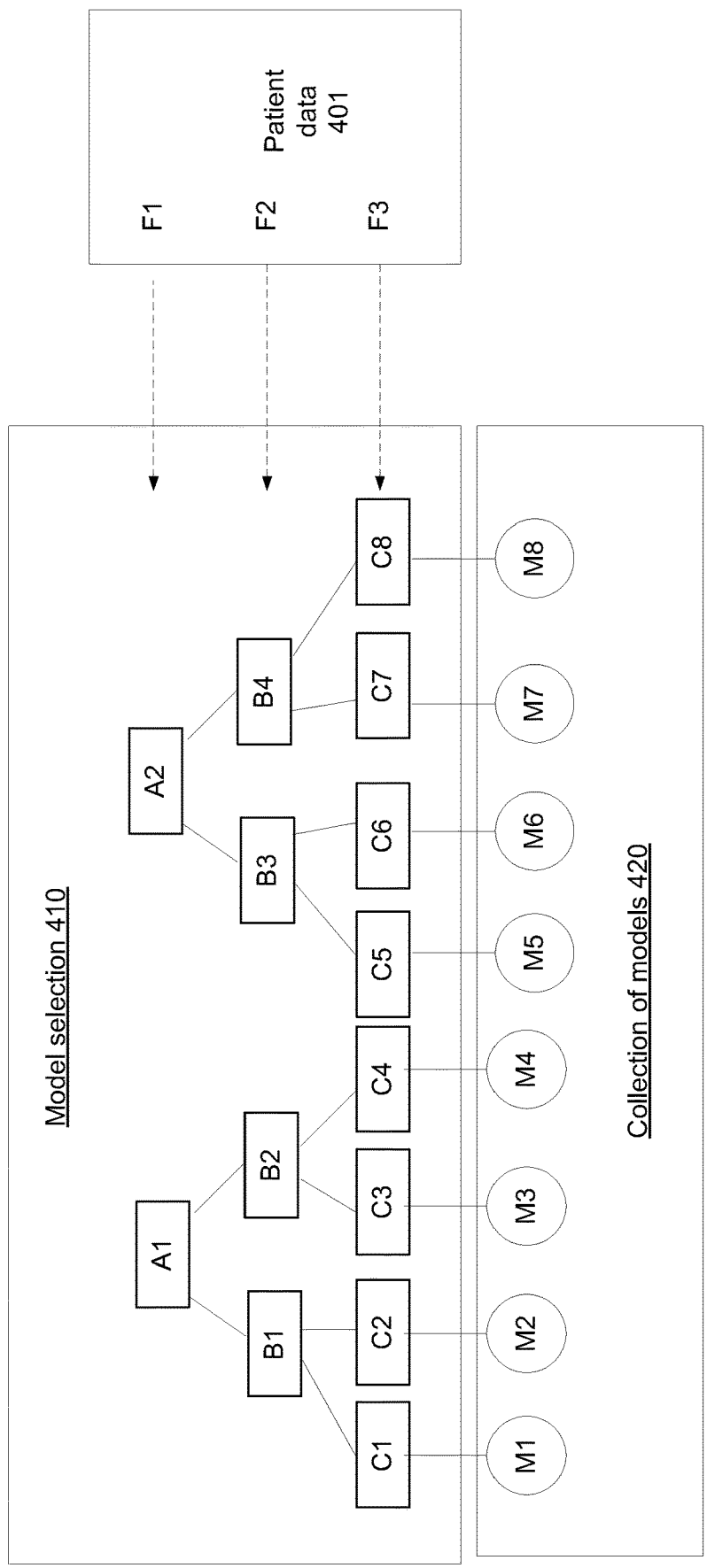
FIG. 4A is a diagram illustrating an exemplary configuration of an integrated model including a hierarchy of decision levels for predictive model selection in accordance with an embodiment of the present disclosure.

FIG. 4A is a diagram illustrating an exemplary configuration of an integrated model 400 including a hierarchy of decision levels for predictive model selection in accordance with an embodiment of the present disclosure. In the illustrated embodiment, the integrated model includes a collection of models 420 at the bottom level and a plurality of decision levels, e.g., A, B, C, each corresponding to a respective feature set in the patient data and each feature set corresponding to one or more features in the patient data. Each decision level includes multiple predefined divisions, or categories, of a respective feature set. For example, level A may correspond to feature F1, e.g., the type of organ to be treated with A1 representing prostate and A2 representing head-neck. Level B may correspond to F2, e.g., size of target, with B1 and B3 representing a range of less than 3 mm, and B2 and B4 representing a range of equal to or greater than 3 mm. As shown, a division in a subordinate decision level is nested with a division in a superordinate decision level, e.g., B1 and B2 are nested with A1, and C1 and C2 are nested with B1.

Provided with patient data 401, e.g., with feature sets F1, F2 and F3, the model selection component 410 can identify one or more applicable divisions from each level based on the patient data of each correspond feature set, starting from the top level. Then one or more predictive model can be selected based on the identified applicable divisions.

FIG. 4B is a flow charge depicting an exemplary method 450 of selecting a suitable predictive model in a hierarchical model in accordance with an embodiment of the present disclosure. The hierarchical model may be implemented as illustrated in FIG. 4B. At 451, a first category is identified on the top level based on the patient data of the first feature corresponding to the top level. At 452, a second category is identified on the second level based on the patient data of the second feature corresponding to the second level. The second category is nested with the first category. At 453, a third category is identified on the third level based on the patient data of the second feature corresponding to the third level. The third category is nested with the third category. At 454, a suitable predictive model can be identified that is applicable in all the identified categories.

In some embodiments more than one suitable predictive model may be identified in a similar process as described with reference to FIG. 4B, and the resulted multiple predictions can be evaluated as described with reference to FIG. 3B.

The hierarchical model in accordance with the present disclosure may either be constructed manually or automatically combining existing configured predictive models, or automatically configuring a set of sub-models from a single training set. For example, a large training set could first be divided into subsets using a clustering algorithm and then each subset would be used as a training set for regression model.

Figure 5:
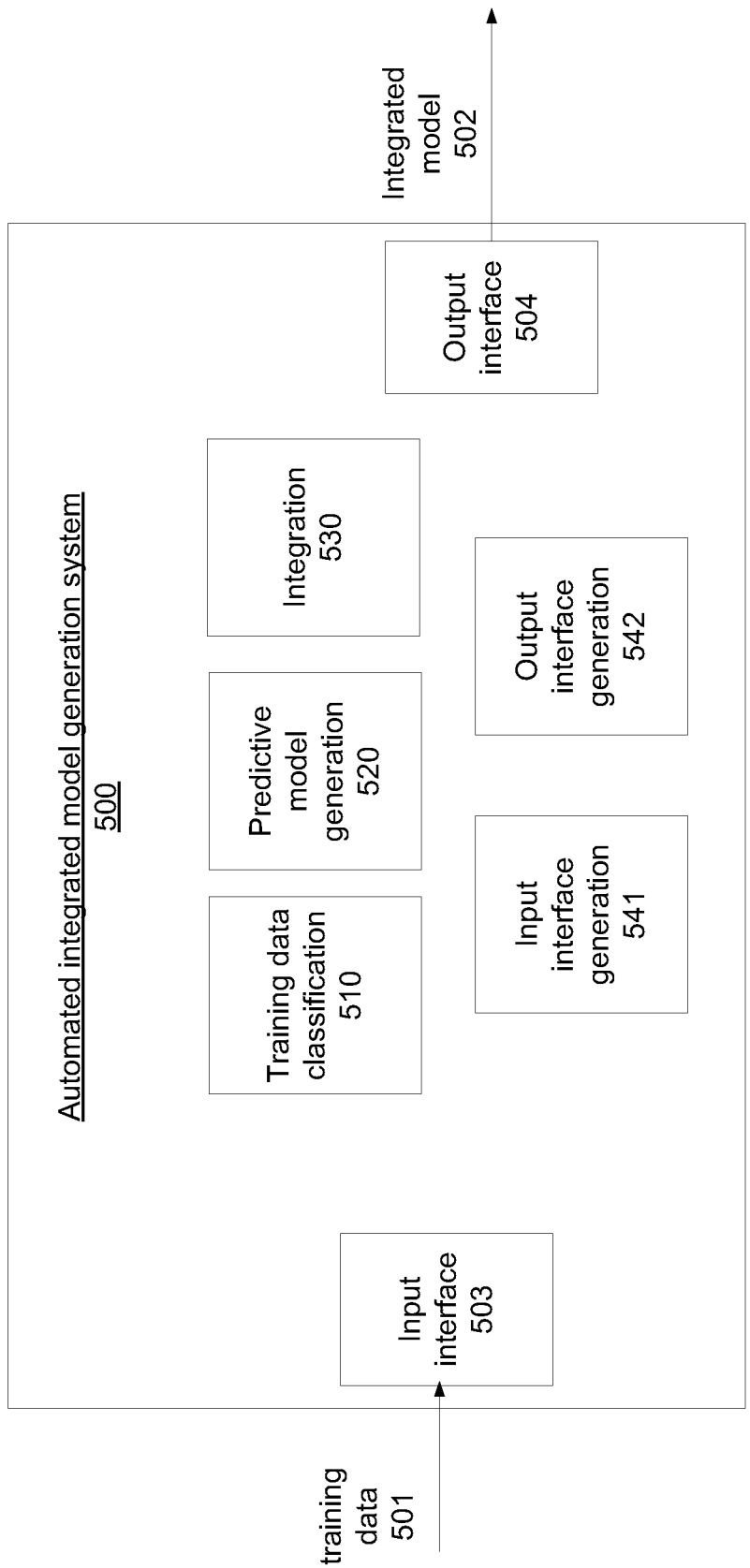
FIG. 5 is a function block diagram illustrating an automated integrated model generation system in accordance with an embodiment of the present disclosure.

FIG. 5 is a function block diagram illustrating an automated integrated model generation system 500 in accordance with an embodiment of the present disclosure. The integrated model generation system 500 includes an input interface 503, a training data classification module 510, a sub-model generation module 520, an integration module 530, an input interface generation module 541, an output interface generation module 541, and an output interface 504. During operation, the system 500 can process the training data 501 received at the input interface 503, generate an integrated model, and output the integrated model 502 through the output interface 504. The integrated model integrates the plurality of predictive models and is operable to select one or more predictive sub-model based on a particular set of patient data, e.g., new patient data, and outcome a therapy prediction. The sub-models in an integrated model may or may not have internal hierarchy regarding the relatedness among the sub-models. For example, all sub-models may be serial to each other, and thus, no internal non-trivial hierarchy is present.

The training data classification module 510 is capable of classifying training data 501 into subsets of training data in accordance with a clustering algorithm, e.g., a hierarchical clustering algorithm. Each subset of training data is then provided to the sub-model generation module 520 to automatically generate a sub-model in accordance with any suitable means that is well known in the art. The predictive models are then provided to the integration module 530 and combined into an integrated or hierarchical model in accordance with an embodiment of the present disclosure. The interface generation modules 541 and 542 can generate an input interface and output interface respectively.

In some embodiments, an integrated model may be enlarged incrementally by configuring new predictive models into a bit different regions. It may also be used to create a prediction scheme for reducing region.

Figure 6:
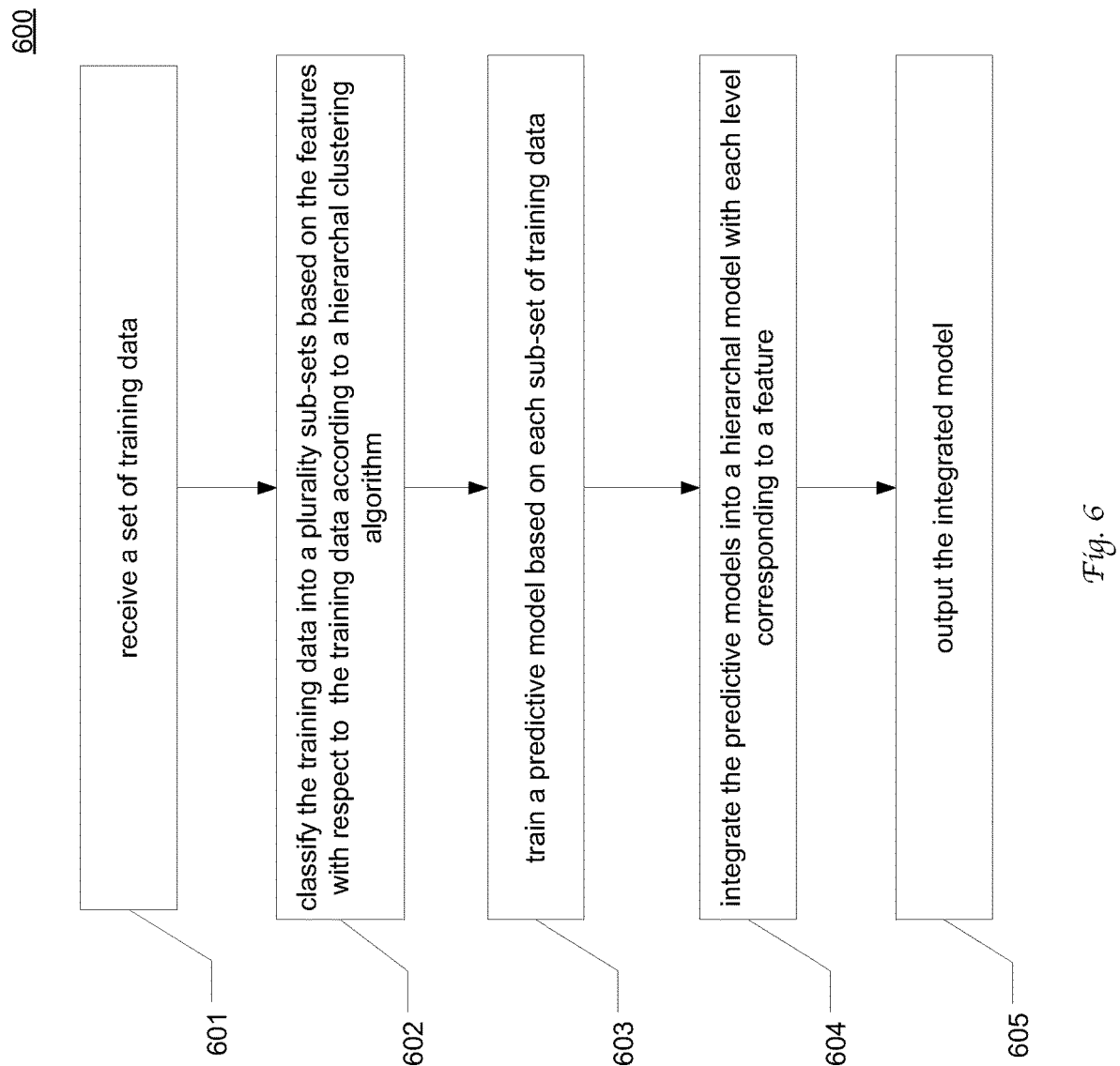
FIG. 6 is a flow chart depicting an exemplary method of automatically generating an integrated model for therapy planning in accordance with an embodiment of the present disclosure.

FIG. 6 is a flow chart depicting an exemplary method 600 of automatically generating an integrated model for therapy planning in accordance with an embodiment of the present disclosure. At 601, a set of training data is received. At 602, the training data is classified into a plurality of subsets of data based on features in the training data in accordance with a hierarchical clustering algorithm, or any other suitable algorithm that is well known in the art. In some embodiments, one case in the training set may be part of only one sub-set, e.g., in a hierarchical integrated model. At 603, a predictive sub-model is trained based on each subset of the training data and operable to generate a radiation treatment prediction, such as in accordance with a regression analysis technique, or in accordance with any other data fit technique that is well known in the art. At 604, the trained predictive models are integrated into a hierarchical model with each level corresponding to a feature set. At 604, the integrated model is output. As will be appreciated by those skilled in the art, a training process generally can be may be used to calibrate certain theoretical and general model to provide as good match as possible in the training set between the prediction and the actual dosimetric outcome. During a training process, a set of selected cases (separate patient data), the training set, may be used to define values of the free parameters of the model, or a model may be created from previously known cases. Once a model is trained, it becomes a particular model that can be used to give reliable predictions to a new patient case, e.g., with unknown dosimetric outcome.

Figure 7:
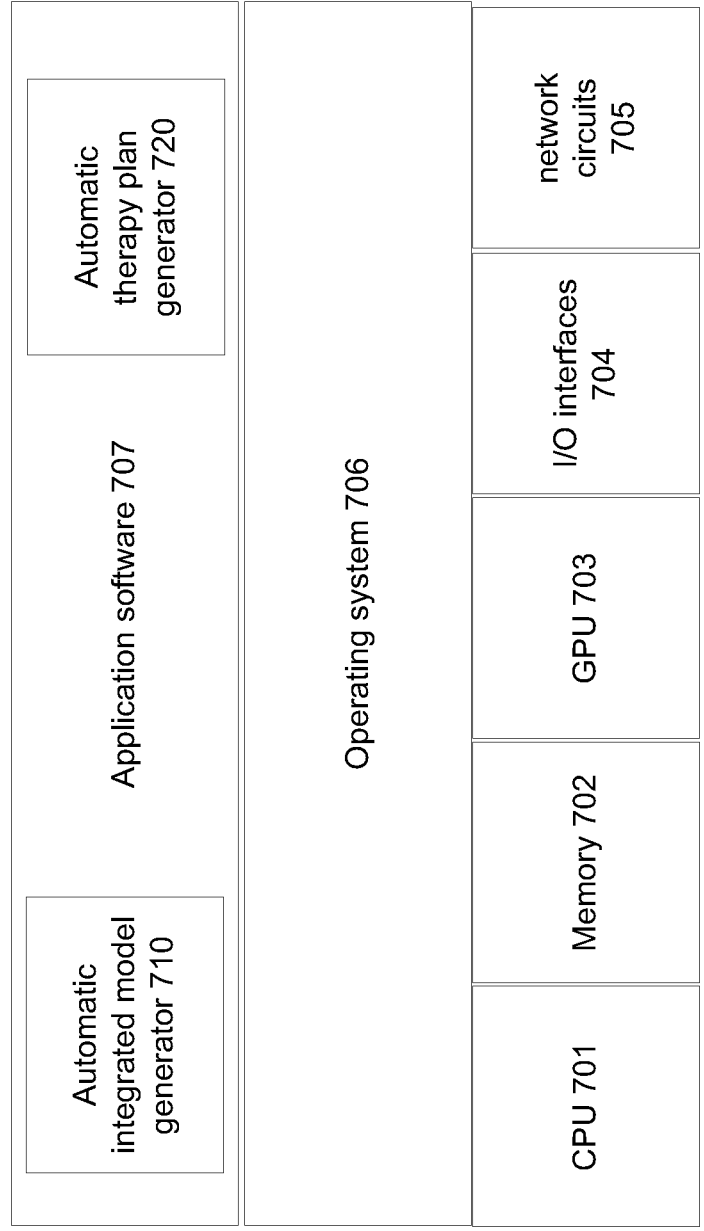
FIG. 7 is a block diagram illustrating an exemplary computing system including an automatic integrated model generator and an automatic therapy plan generator in accordance with an embodiment of the present disclosure.

FIG. 7 is a block diagram illustrating an exemplary computing system 700 including an automatic integrated model generator 710 and an automatic therapy plan generator 720 in accordance with an embodiment of the present disclosure. The computing system 700 comprises a processor 701, a system memory 702, a GPU 703, I/O interfaces 704 and network circuits 705, an operating system 706 and application software 707 including an automatic integrated model generator 710 and an automatic therapy plan generator 720 stored in the memory 702. In some other embodiments, an automatic integrated model generator and an automatic therapy plan generator can be implemented in two separate systems.

When incorporating the input and configuration input, e.g. training data, and executed by the CPU 701, the automatic integrated model generator 710 can automatically generate an integrated model encompassing a plurality of predictive models trained by the training data in accordance with an embodiment of the present disclosure. The automatic integrated model generator 710 may perform various other functions as discussed in details with reference to FIG. 5 and FIG. 6.

When incorporating the input and configuration input, e.g. a set of patient data, and executed by the CPU 701, the automatic therapy plan generator 720 can automatically generate treatment planning parameters by an automatically selected predictive model in accordance with an embodiment of the present disclosure. The automatic therapy plan generator 720 may perform various other functions as discussed in details with reference to FIGS. 1, 2, 3A, 3B, 4A and 4B.

As will be appreciated by those with ordinary skill in the art, the automatic integrated model generator 710 and the automatic therapy plan generator 720 can be a software implemented in any one or more suitable programming languages that are known to those skilled in the art, such as C, C++, Java, Python, Perl, C#, SQL, etc.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A computer implemented method of automatically generating a radiation treatment plan for a patient, said method comprising:
   accessing patient information;
   accessing an integrated dose prediction model that integrates a plurality of predictive models, wherein said integrated dose prediction model is a hierarchical model comprising said plurality of predictive models arranged in a hierarchy, wherein a respective predictive model of said plurality of predictive models correlates input variables of patient information features with output variables pertinent to radiation treatment planning to predict an achievable dose distribution in said patient;
   automatically selecting one or more predictive models based on said patient information in accordance with said integrated dose prediction model;
   processing said patient information in accordance with said one or more predictive models; and
   outputting, by said one or more predictive models, a resultant radiation treatment prediction comprising a predicted achievable dose distribution in said patient.

2. The computer implemented method of claim 1, wherein said automatically selecting and said processing comprise:
   generating radiation treatment predictions based on said patient information using said plurality of predictive models;
   evaluating said radiation treatment predictions; and
   selecting said one or more predictive models based on said evaluating.

3. The computer implemented method of claim 2, wherein said evaluating comprises evaluating parameters representing reliability, complexity, and probability with respect to said radiation treatment predictions.

4. The computer implemented method of claim 1, wherein said patient information comprises data of a plurality of sets of features, each set of said plurality of sets comprising one or more features,
   wherein each of said plurality of predictive models is associated with a respective division with respect to each set of features of said plurality of sets of features, and
   wherein said automatically selecting comprises:
      identifying a corresponding division in each set of features based on said patient information; and
      selecting said one or more predictive models based on identified divisions of said plurality of sets of features.

5. The computer implemented method of claim 4, wherein said hierarchy comprises a plurality of intermediate levels and a lowest level, wherein said lowest level comprises said plurality of predictive models, wherein each intermediate level corresponds to divisions with respect to a respective set of features, and wherein divisions corresponding to a subordinate intermediate level are nested with divisions corresponding to a superordinate intermediate level.

6. The computer implemented method of claim 4, wherein said plurality of sets of features are selected from a group consisting of organ type, organ dimension descriptions, target location, target size, geometric characterizations of one or more organs at risk proximate to a target volume.

7. The computer implemented method of claim 1, wherein said integrated dose prediction model is generated by automatically classifying said plurality of predictive models based on previous clinical data in accordance with a clustering algorithm.

8. The computer implemented method of claim 1, wherein each predictive model of said plurality of predictive models is automatically established through a machine training process in accordance with a regression method and based on previous clinical data.

9. A non-transitory computer-readable storage medium embodying instructions that, when executed by a processing device, cause the processing device to perform a method of automatically generating an integrated dose prediction model for planning radiation therapy, said method comprising:
   accessing a plurality of predictive models, wherein each of said plurality of predictive models correlates input variables representing patient information features with variables pertinent to radiation treatment planning to predict an achievable dose distribution in a patient; and
   integrating said plurality of predictive models into said integrated dose prediction model, wherein said integrated dose prediction model is a hierarchical model comprising said plurality of predictive models arranged in a hierarchy, wherein said integrated dose prediction model is configured to:
      receive data of said patient information features;
      automatically select one or more predictive models from said plurality of predictive models based on said data of said patient information features; and
      process said data of said patient information features in accordance with said one or more predictive models to output a resultant radiation treatment prediction comprising a predicted achievable dose distribution in said patient.

10. The non-transitory computer-readable storage medium of claim 9, wherein said method further comprises:
    configuring an input interface operable to receive said data of said patient information features; and
    configuring an output interface operable to output said resultant radiation treatment prediction.

11. The non-transitory computer-readable storage medium of claim 10, wherein said patient information features are selected from a group consisting of organ identification, organ dimension descriptions, target location, target size, and geometric characterizations of one or more organs at risk proximate to a target volume.

12. The non-transitory computer-readable storage medium of claim 9, wherein said integrating comprises associating an applicable category with each of said patient information features for each predictive model of said plurality of predictive models.

13. The non-transitory computer-readable storage medium of claim 12, wherein said hierarchy comprises a bottom level and one or more decision levels, wherein said bottom level comprises said plurality of predictive models, and wherein said one or more decision levels are operable to automatically select said one or more predictive models from said bottom level based on applicable categories associated with said data of said patient information features.

14. The non-transitory computer-readable storage medium of claim 9, wherein said method further comprises:
    accessing training data; and
    generating said plurality of predictive models based on said training data in a machine training process, wherein a respective predictive model of said plurality of predictive models is generated in accordance with an algorithm selected from a group consisting of a linear regression algorithm, a classification algorithm, a decision tree algorithm, a segmentation algorithm, an association algorithm, a sequence clustering algorithm, and a combination thereof.

15. The non-transitory computer-readable storage medium of claim 14, wherein said method further comprises classifying said training data into subsets of training data in accordance with a clustering algorithm, and wherein said generating said plurality of predictive models comprises configuring a predictive model based on a subset of training data.

16. A system comprising:
    a processor;
    a memory coupled to said processor and comprising instructions that, when executed by said processor, cause the processor to perform a method of automatically generating a radiation therapy plan, said method comprising:
        accessing patient information;
        accessing an integrated dose prediction model that integrates a plurality of predictive models, wherein said integrated dose prediction model is a hierarchical model comprising said plurality of predictive models arranged in a hierarchy, wherein a respective predictive model of said plurality of predictive models correlates input variables of patient information features with output variables pertinent to radiation treatment planning to predict an achievable dose distribution in a patient;
        automatically selecting one or more predictive models based on said patient information in accordance with said integrated dose prediction model;
        processing said patient information in accordance with said one or more predictive models; and
        outputting, by said one or more predictive models, a resultant radiation treatment prediction comprising a predicted achievable dose distribution in said patient.

17. The system of claim 16, wherein said automatically selecting and said processing comprise:
    generating radiation treatment predictions based on said patient information using said plurality of predictive models;
    evaluating said radiation treatment predictions; and
    selecting said one or more predictive models based on said evaluating.

18. The system of claim 16, wherein said patient information comprises data of a plurality of sets of features, each set of said plurality of sets comprising one or more features,
    wherein each predictive model of said plurality of predictive models is associated with a respective division with respect to each set of features of said plurality of sets of features, and
    wherein said automatically selecting comprises:
        identifying a corresponding division in each set of features based on said patient information; and
        selecting said one or more predictive models based on identified divisions of said plurality of sets of features.

19. The system of claim 18, wherein said plurality of sets of features are selected from a group consisting of organ type, organ dimension descriptions, target location, target size, geometric characterizations of one or more organs at risk proximate to a target volume, and wherein said resultant radiation treatment prediction comprises a predicted achievable dose distribution.

* * * * *